United States Patent [19]

Henson et al.

[11] 4,294,774

[45] Oct. 13, 1981

[54] PREPARATION OF ORGANIC ISOCYANATES

[75] Inventors: Thomas R. Henson; John F. Timberlake, both of Baton Rouge, La.

[73] Assignee: The Dow Chemical Company, Midland, Mich.

[21] Appl. No.: 206,747

[22] Filed: Nov. 14, 1980

[51] Int. Cl.³ .......................................... C07C 118/00
[52] U.S. Cl. ................................................. 260/453 P
[58] Field of Search ..................................... 260/453 P

[56] References Cited

U.S. PATENT DOCUMENTS

| | | | |
|---|---|---|---|
| 3,763,217 | 10/1973 | Brill | 560/24 |
| 3,919,279 | 11/1975 | Rosenthal et al. | 260/453 P |
| 3,962,302 | 6/1976 | Rosenthal et al. | 260/453 P |
| 4,081,472 | 3/1978 | Tsumura et al. | 260/453 P |

FOREIGN PATENT DOCUMENTS 52-19624  2/1977  Japan .

OTHER PUBLICATIONS

Mukaiyama et al., *J. Am. Chem. Soc.*, vol. 78, pp. 1946–1948 (1956).
Mukaiyama et al., *J. Chem. Soc. Japan*, vol. 33 (8), pp. 1137–1143 (1960).
Griffin et al., *I & EC Product Research and Development*, vol. 1 (4), pp. 265–268 (1962).

*Primary Examiner*—Dolph H. Torrence
*Attorney, Agent, or Firm*—A. J. Young

[57] ABSTRACT

A process for the preparation of an organic isocyanate by preparing a heated solution of an alkyl carbamate in a N,N-dialkyl aniline compound solvent which is catalytic with respect to the rate of decomposition of the carbamate but unreactive with respect to the organic isocyanate decomposition product.

5 Claims, No Drawings

PREPARATION OF ORGANIC ISOCYANATES

BACKGROUND OF THE INVENTION

The present invention relates to the preparation of organic isocyanates. More particularly, this invention relates to the preparation of organic isocyanates by the thermal decomposition of alkyl carbamates dissolved in a solvent which also acts as a catalyst with respect to the decomposition reaction.

Organic isocyanates are useful chemical intermediates. In particular, aromatic diisocyanates are important intermediates because they can be reacted with polyols to produce polyurethanes. A U.S. Pat. No. 3,962,302 shows that alkyl carbamates can be thermally decomposed to isocyanates in the absence of a solvent, but the product selectivity of this process is too low to make it successful commercially. In addition, the patent shows that inert solvents for the carbamates can be used to improve on the product selectivity of the thermal decomposition reaction. However, the rate of decomposition to the isocyanates is relatively slow when inert solvents are used.

SUMMARY

According to the method of the present invention, the problem of slow rate of decomposition when an inert solvent is used for the carbamate can be overcome by providing a solvent that is characterized as being catalytic to the rate of reaction of the carbamate but unreactive with respect to the desired isocyanate product produced.

In general, the present invention provides a process for preparing organic isocyanates from alkyl carbamates. The organic substituent of the organic isocyanate produced can be either an alkyl or aryl group and is characterized as being attached to the nitrogen atom of the corresponding starting alkyl carbamate. In addition, the alkyl group of the alkyl carbamate is characterized as having less than four carbon atoms, since it is known that alkyl carbamates which have an alkyl group with four or more carbon atoms rearrange during decomposition to produce carbon dioxide, the corresponding alkyl alcohol or diol, and amine or urea residues.

The present process comprises the step of preparing a heated solution of an alkyl carbamate in a solvent, whereby the carbamate is catalytically decomposed into the corresponding isocyanate and alkyl alcohol, said solvent being catalytic with respect to the rate of decomposition of the carbamate but unreactive with respect to the isocyanate produced. Solvents useful in practicing the present method are basic (proton-accepting) compounds of nitrogen which do not include an active hydrogen atom. Examples of such solvents are tertiary amines wherein one group is a phenyl group and the other two are alkyl groups where either alkyl group is a methyl or ethyl group.

In the practice of the present method, it has been found that, although tri-alkyl amines are strong bases and very effective catalysts with respect to the rate of decomposition of carbamates, they are undesirable for the purposes of the present method because they further act as catalysts to cause the desired isocyanate products to rapidly react to form higher isocyanate derivatives. The inclusion of one phenyl group in the tertiary amine solvent substantially overcomes this problem without substantially reducing the catalytic effect of the solvent on the rate of decomposition of the carbamate to the isocyanate. On the other hand, it has also been found that if tertiary amine solvents with a second phenyl group or larger alkyl groups, i.e., butyl groups, are used, the catalytic rate of decomposition effect of the solvents is substantially reduced.

The thermal decomposition of the present method is carried out between about 150° C. and about 350° C., and preferably between about 175° C. and about 275° C. In addition, it is immaterial how the heated solution is prepared. It may, for example, be prepared by dissolving the carbamate in the solvent and then heating the solution to the desired temperature. Alternatively, it may be prepared by adding the carbamate to the solvent which has been preheated to the desired temperature. A third alternative would be the addition of the carbamate to the solvent at a temperature between ambient and that of the chosen reaction temperature and heating the solution to the reaction temperature. All of these variations may be employed, as well as many others which will occur to those skilled in the art. It is essential, however, that the solvent be catalytic with respect to the thermal decomposition of carbamates but unreactive with respect to the organic isocyanates produced by the decomposition reaction.

It is an object of this invention to provide a process for the production of organic isocyanates. It is a further object of this invention to provide a process for the production of organic isocyanates by the thermal decomposition of the corresponding alkyl carbamates which have been organically substituted on the nitrogen atom. It is a further object of this invention to provide a process for the production of organic isocyanates wherein a solvent is used which acts as a catalyst with respect to the rate of the decomposition reaction without substantially affecting the selectivity of the reaction. Other objects of the invention will be apparent to those skilled in the art from the more detailed description which follows.

DESCRIPTION OF THE PREFERRED EMBODIMENT

The following description illustrates the manner in which the principles of this invention are applied, but is not to be construed as in any manner limiting the scope of the invention.

More specifically, the present method comprises preparing a heated solution of the alkyl carbamate in the solvent, thereby thermally and catalytically decomposing the carbamate into the corresponding organic isocyanate and alkyl alcohol. The isocyanate, solvent, and alcohol are then further separated by distillation, inert gas stripping, crystallization or other known means, and the isocyanate recovered as the desired reaction product. Beneficially, N,N-dialkyl anilines are employed as the solvents, with N,N-dimethyl aniline, N-N-diethyl aniline, N-methyl-N-ethyl aniline or mixtures thereof most preferred.

The invention is further illustrated by the following examples according to the invention, Examples 1–3, and comparative examples using non-catalytic inert solvents, Examples 4 and 5.

EXAMPLE 1

Five grams (0.0176 moles) of methylene dimethyl diphenyl dicarbamate were dissolved in 100.7 grams of N,N-dimethylaniline. The solution was then heated to and refluxed in a reflux condenser at 195° C. Samples of the reactor mixture were taken periodically and analyzed by gel-permeation chromatography. The results of this example are shown in Table 1.

EXAMPLE 2

Five grams (0.0176 moles) of methylene dimethyl diphenyl dicarbamate were dissolved in 100 grams of N,N-diethyl aniline. The solution was then heated to 200° C. Periodic samples were taken and analyzed as in Example 1. The results of this example are shown in Table 1.

EXAMPLE 3

Two and one-half grams (0.0088 moles) of methylene dimethyl diphenyl dicarbamate were dissolved in 50 grams of diphenyl methyl amine. The solution was then heated to 200° C. Periodic samples were taken and analyzed as in Example 1. The results of this example are shown in Table 1.

EXAMPLE 4

Five grams (0.0176 moles) of methylene dimethyl diphenyl dicarbamate was dissolved in 101.3 grams of diethyl phthalate. The solution was then heated to 200° C. Periodic samples were taken and analyzed as in Example 1. The results of this example are shown in Table 1.

EXAMPLE 5

This example was carried out following the procedures of Example 1. Five grams of methylene dimethyl diphenyl dicarbamate was dissolved in about 100 grams of diphenyl oxide and then heated to 210° C. The results are shown in Table 1.

TABLE 1

COMPOSITION OF REACTION MIXTURE (MOLE PERCENT - EXCLUDING SOLVENT)

| | Example 1 N,N-dimethyl Aniline | | | Example 2 N,N-diethyl Aniline | | | Example 3 diphenylmethyl Amine | | |
|---|---|---|---|---|---|---|---|---|---|
| Time (Hrs.) | Di Carbamate | Carbamate/ Iso-Cyanate | Di Iso-Cyanate | Di Carbamate | Carbamate/ Iso-Cyanate | Di Iso-Cyanate | Di Carbamate | Carbamate/ Iso-Cyanate | Di Iso-Cyanate |
| 0 | 100 | 0 | 0 | 100 | 0 | 0 | 100 | 0 | 0 |
| 1 | — | — | — | 56.9 | 36.9 | 5.9 | 96.6 | 3.2 | 0.2 |
| 2 | — | — | — | 48.9 | 42.0 | 8.5 | 86.5 | 12.8 | 0.7 |
| 3 | — | — | — | 44.1 | 44.7 | 10.4 | 80.9 | 17.7 | 1.4 |
| 3.4 | — | — | — | — | — | — | — | — | — |
| 4.0 | 18 | 44 | 27 | — | — | — | — | — | — |
| 5.0 | — | — | — | — | — | — | 72.2 | 25.2 | 2.6 |
| 5.4 | — | — | — | — | — | — | — | — | — |
| 8 | 6 | 33 | 36 | — | — | — | — | — | — |
| 12 | 2 | 26 | 42 | — | — | — | — | — | — |
| 16 | 0 | 22 | 44 | — | — | — | — | — | — |
| 24 | 0 | 18 | 46 | 16.2 | 45.4 | 29.7 | — | — | — |

| | Example 4 Diethyl Phthalate | | | Example 5 Diphenyl Oxide | | |
|---|---|---|---|---|---|---|
| Time (Hrs.) | Di Carbamate | Carbamate/ Iso-Cyanate | Di Iso-Cyanate | Di Carbamate | Carbamate/ Iso-Cyanate | Di Iso-Cyanate |
| 0 | 100 | 0 | 0 | 100 | 0 | 0 |
| 1 | — | — | — | — | — | — |
| 2 | — | — | — | — | — | — |
| 3 | — | — | — | — | — | — |
| 3.4 | — | — | — | 62.5 | 33 | 4.5 |
| 4.0 | 51 | 33 | 13 | — | — | — |
| 5.0 | — | — | — | — | — | — |
| 5.4 | — | — | — | 46 | 44 | 10 |
| 8 | 31 | 38 | 20 | — | — | — |
| 12 | 23 | 39 | 24 | — | — | — |
| 16 | — | — | — | — | — | — |
| 24 | 15 | 37 | 28 | — | — | — |

As shown by the above examples (Examples 1 and 2, Table 1), a much faster rate of decomposition of the carbamate into the intermediate carbamateisocyanate and diisocyanate was observed for the method of this invention which employs catalytic solvents, than for the uncatalyzed method illustrated in the comparative Examples 4 and 5, even though the decomposition rate would be expected to be higher for Example 5 because of the slightly higher temperature. In addition, Example 3 illustrates the undesirable effect of a second phenyl group in the tertiary amine solvent.

While certain representative embodiments and details have been shown for the purpose of illustrating this invention, it will be apparent to those skilled in the art that various changes and modifications can be made therein without departing from the spirit and scope of the invention.

What is claimed is:

1. A process for the preparation of an organic isocyanate product comprising the step of preparing a heated solution of an alkyl carbamate in a solvent whereby the carbamate is catalytically decomposed into the corresponding organic isocyanate product and alkyl alcohol, said solvent being an N,N-dialkyl aniline compound which is characterized as being catalytic with respect to the decomposition rate of the carbamate but unreactive with respect to the organic isocyanate product.

2. The process of claim 1, wherein the N,N-dialkyl aniline is N,N-dimethyl aniline, N,N-diethyl aniline, N-methyl-N-ethyl aniline or mixtures thereof.

3. The process of claim 2, wherein the carbamate is methylene dimethyl diphenyl carbamate.

4. The process of claim 3, wherein the heated solution is prepared by dissolving the carbamate in the solvent and then heating the solution to a temperature of between about 150° C. and about 350° C.

5. The process of claim 3, wherein the heated solution is prepared by adding the carbamate to the solvent which has been preheated to a temperature of between about 150° C. and about 350° C.

* * * * *